US008747309B2

(12) United States Patent
Viola

(10) Patent No.: US 8,747,309 B2
(45) Date of Patent: Jun. 10, 2014

(54) SUSPENSION SYSTEM FOR MINIMALLY INVASIVE SURGERY

(75) Inventor: Frank Viola, Sandy Hook, CT (US)

(73) Assignee: Covidien LP, Manfield, MA (US)

(*) Notice: Subject to any disclaimer, the term of this patent is extended or adjusted under 35 U.S.C. 154(b) by 248 days.

(21) Appl. No.: 13/209,529

(22) Filed: Aug. 15, 2011

(65) Prior Publication Data

US 2012/0116173 A1    May 10, 2012

Related U.S. Application Data

(60) Provisional application No. 61/411,515, filed on Nov. 9, 2010.

(51) Int. Cl.
*A61B 1/32* (2006.01)

(52) U.S. Cl.
USPC .......................................................... 600/227

(58) Field of Classification Search
USPC .......... 600/201–234; 606/130; 248/68.1, 200, 248/288.11
See application file for complete search history.

(56) References Cited

U.S. PATENT DOCUMENTS

| 4,254,763 | A | * | 3/1981 | McCready et al. ........... 600/230 |
|---|---|---|---|---|
| 5,281,232 | A | | 1/1994 | Hamilton et al. |
| 5,474,056 | A | | 12/1995 | Laborie et al. |
| 5,501,653 | A | | 3/1996 | Chin |
| 5,690,607 | A | | 11/1997 | Chin et al. |
| 5,820,623 | A | | 10/1998 | Ng |
| 5,961,527 | A | | 10/1999 | Whitmore, III et al. |
| 6,221,082 | B1 | | 4/2001 | Marino et al. |
| 6,514,239 | B2 | | 2/2003 | Shimmura et al. |
| 6,589,254 | B2 | | 7/2003 | Fontenot |
| 6,949,105 | B2 | | 9/2005 | Bryan et al. |
| 7,189,246 | B2 | | 3/2007 | Otsuka et al. |
| 2002/0007188 | A1 | | 1/2002 | Arambula et al. |
| 2005/0075536 | A1 | | 4/2005 | Otsuka et al. |
| 2005/0165449 | A1 | | 7/2005 | Cadeddu et al. |
| 2005/0245928 | A1 | * | 11/2005 | Colleran et al. ................ 606/61 |
| 2005/0256371 | A1 | | 11/2005 | Schara et al. |
| 2006/0149135 | A1 | | 7/2006 | Paz |
| 2007/0073102 | A1 | | 3/2007 | Matsuno et al. |
| 2007/0299387 | A1 | | 12/2007 | Williams et al. |

(Continued)

FOREIGN PATENT DOCUMENTS

| EP | 2286756 A | 2/2011 |
|---|---|---|
| EP | 2329787 A2 | 6/2011 |

(Continued)

OTHER PUBLICATIONS

Extended European Search Report dated Jun. 25, 2013 from corresponding European Application No. 11188196.7 (14 pgs.).

*Primary Examiner* — Mary Hoffman
*Assistant Examiner* — Tara Carter

(57) ABSTRACT

A suspension system for supporting surgical devices inside a patient's body cavity comprising an external frame, a plurality of elongated members extending from the external frame and through the patient's skin into the body cavity, and an internal platform located inside the body cavity. The internal platform includes a plurality of links reconfigurable from a first elongated position wherein the links are substantially aligned along a longitudinal axis for insertion to a second position wherein the links are angled with respect to one another to form a non-linear configuration. A first support of the external frame is movable with respect to the second support to thereby move the internal platform.

17 Claims, 12 Drawing Sheets

(56) References Cited

U.S. PATENT DOCUMENTS

| | | |
|---|---|---|
| 2008/0004634 A1 | 1/2008 | Farritor et al. |
| 2008/0058835 A1 | 3/2008 | Farritor et al. |
| 2008/0071290 A1 | 3/2008 | Larkin et al. |
| 2008/0188869 A1 | 8/2008 | Weitzner et al. |
| 2008/0221591 A1 | 9/2008 | Farritor et al. |
| 2009/0048612 A1 | 2/2009 | Farritor et al. |
| 2009/0054909 A1 | 2/2009 | Farritor et al. |
| 2012/0221063 A1* | 8/2012 | Abdou ......... 606/86 A |

FOREIGN PATENT DOCUMENTS

| | | |
|---|---|---|
| EP | 2329789 A1 | 6/2011 |
| WO | WO 2006/058221 A2 | 6/2006 |
| WO | WO 2009/023851 A1 | 2/2009 |

* cited by examiner

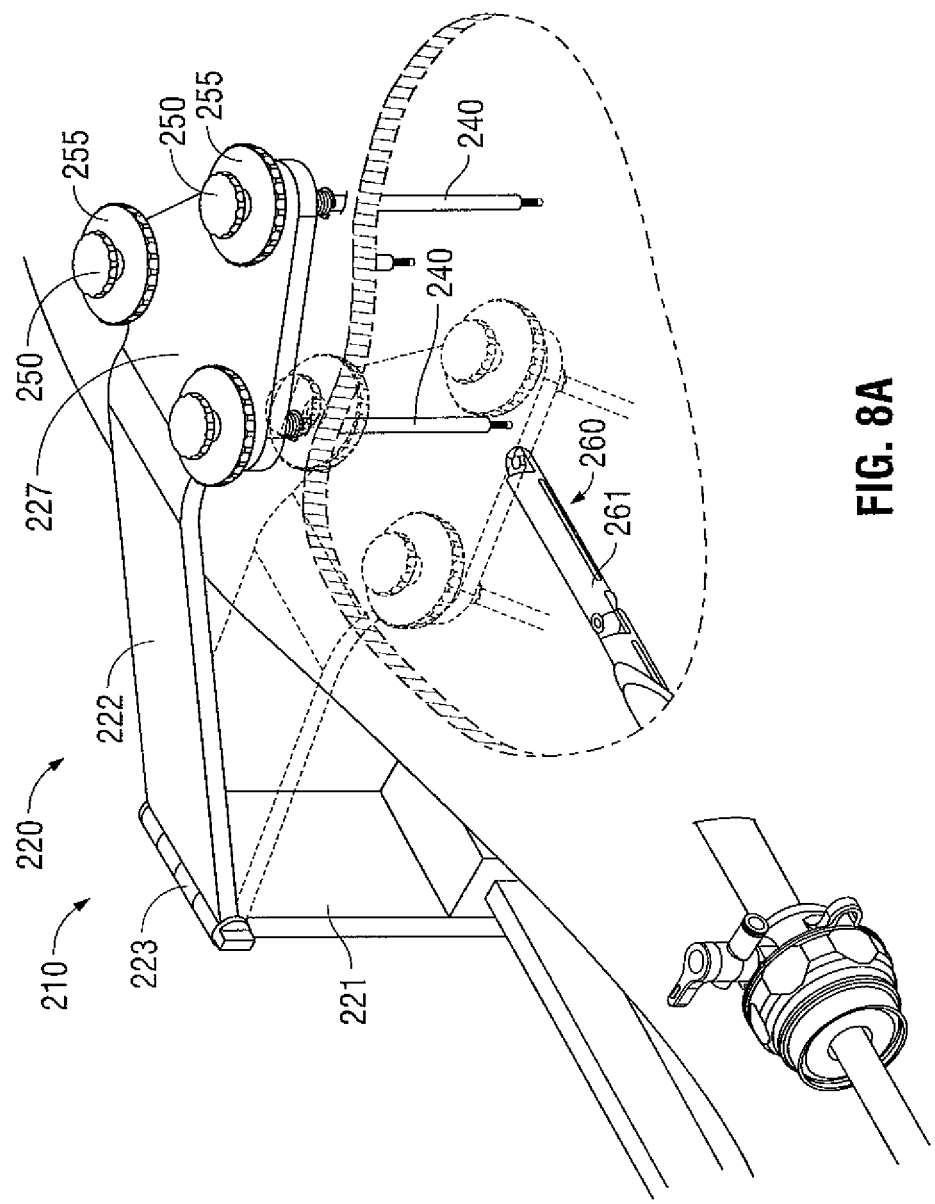

SUSPENSION SYSTEM FOR MINIMALLY INVASIVE SURGERY

CROSS REFERENCE TO RELATED APPLICATION

The present application claims the benefit of and priority to U.S. Provisional Application Ser. No. 61/411,515 filed on Nov. 9, 2010, the entire contents of which are incorporated herein by reference.

TECHNICAL FIELD

This application generally relates to the field of minimally invasive surgery. More particularly, the present disclosure relates to a system for supporting a plurality of instruments for minimally invasive surgery.

RELATED ART

Laparoscopy is a minimally invasive surgical procedure performed in the abdominal cavity. It has become the treatment of choice for several routinely performed interventions.

However, known laparoscopy technologies are limited in scope and may be unduly complex due in part to 1) mobility restrictions resulting from using rigid tools inserted through access ports, and 2) limited visual feedback. That is, long rigid laparoscopic tools inserted through small incisions in the abdominal wall or other regions of laparoscopic surgery limit the surgeon's range of motion and therefore may increase the complexity of the surgical procedures being performed. Similarly, using a 2-D image from a typically rigid laparoscope inserted through a small incision limits the overall understanding of the surgical environment. Further, in many current surgical procedures, an additional port is required to accommodate a laparoscope (camera), and a port is required for each instrumentation insertion, requiring an additional incision which increases the risk of infection and lengthens patient recovery time. Single port laparoscopic surgery can have restricted instrument mobility.

There is a continuing need in the art for improved surgical methods, systems, and devices for laparoscopic and other minimally invasive surgery.

SUMMARY

The present disclosure pertains to a suspension system for supporting surgical instruments for use inside a body cavity in a minimally invasive surgical procedure, and particularly in a laparoscopic procedure. The suspension system comprises an external frame having a first support and a second support, a plurality of elongated members extending from the external frame and into the body cavity, and an internal platform located inside the body cavity. The internal platform includes a plurality of links reconfigurable from a first elongated position wherein the links are substantially aligned along a longitudinal axis for insertion to a second position wherein the links are angled with respect to one another to form a non-linear configuration. The first support is movable with respect to the second support to thereby move the internal platform.

In one embodiment, the first support includes an elongated arm pivotably attached to the second support for movement toward and away from the body cavity. In another embodiment, the first support includes an elongate arm rotatably attached to the second support for rotation about a longitudinal axis of the second support.

The external frame can include first attachment structure for connecting the elongated members at the proximal portion and the links can include second attachment structure to receive the distal portion of the elongated members. The links can having mounting structure for mounting a surgical device thereto and can be pivotally attached to one another. One of the links can have tool attachment structure for detachable connection to an insertion tool.

In one embodiment, the first support is pivotable from a position substantially horizontal to overlie the patient to a position substantially vertical with respect to the patient.

In another aspect, the present disclosure provides a suspension system for supporting surgical devices inside a patient's body cavity comprising an external frame having a first plurality of holes extending therethrough and attached to a support for movement toward and away from the body cavity, a plurality of rods extending from the frame sized to at least partially extend through one of the plurality of holes, and an internal platform including a series of interconnecting links having at least one hole sized to receive one of the rods therethrough.

The links can include an attachment structure located along the body thereof. The system may further comprise a pod having a complementary attachment structure to an attachment structure of the links. In some embodiments, the external frame is pivotably connected to the rigid support.

Preferably, the links are insertable into the body cavity in a generally elongated position and are reconfigured to an angular position within the body cavity.

The present disclosure also provides in another aspect a suspension system for supporting surgical devices inside a patient's body cavity comprising a substantially rigid external frame positioned outside the body and movably connected to a support for movement with respect to the body cavity, a plurality of elongated connectors extending from the external frame into the body cavity, and an internal support located inside the body cavity and attached to the elongated connectors. The elongated connectors are movable to apply a retraction force on a portion of the internal support to change the plane of the portion with respect to other portions of the support.

The internal support preferably includes a plurality of links reconfigurable from a first elongated position wherein the links are substantially aligned along a longitudinal axis for insertion to a second position wherein the links are angled with respect to one another to form a non-linear configuration for attachment to the elongated connectors.

Preferably, the internal support has instrument receiving structure to mount surgical instruments thereto.

In another aspect, the present disclosure provides a method for providing a platform for surgical instruments for performing minimally invasive surgery, the method comprising the steps of:
  providing an external frame;
  inserting the elongated members into a body cavity of a patient;
  connecting elongated members to the external frame;
  inserting through a different site an internal platform configured in a substantially linear configuration;
  reconfiguring the internal platform inside the body cavity to a non-linear configuration;
  joining the elongated members and the platform inside the body cavity; and
  moving the external frame to move the internal platform within the body cavity.

The step of reconfiguring the platform can include the step of pivoting a series of links with respect to one another. The method may further comprise the step of placing a pod within the body cavity and attaching the pod to one of either the internal platform and one of the elongated members.

BRIEF DESCRIPTION OF THE DRAWINGS

The accompanying drawings, which are incorporated in and form part of the specification, illustrate the present disclosure when viewed with reference to the description, wherein:

FIG. 8A is a partially cut away view of an alternate embodiment of the suspension system illustrating pivoting of the external frame structure and showing insertion of the internal platform inside a body cavity;

Figure 1:
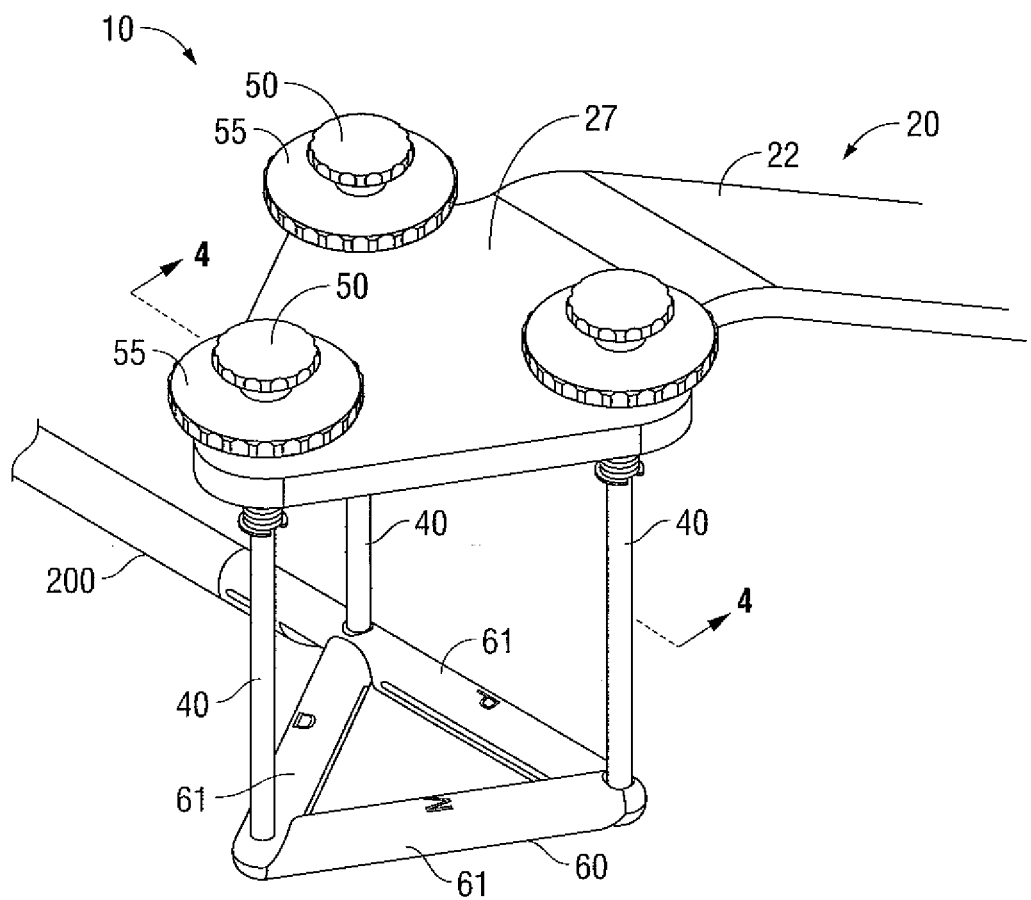
FIG. 1 is a perspective view of a suspension system in accordance with the principles of the present disclosure, illustrating an external frame structure, a plurality of rods, and an internal platform.

Other features of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed suspension system are described in detail with reference to the drawings, in which like reference numerals designate identical or corresponding elements in each of the several views. As used herein, the term "distal" refers to that portion of the suspension system, or component thereof, further from the user while the term "proximal" refers to that portion of that portion of the suspension system or component thereof, closer to the user.

Referring now to the drawings, wherein like reference numerals identify similar structural elements of the subject system, there is illustrated in FIG. 1 a suspension system, designated generally by reference numeral 10 which forms a stable rigid platform for surgical devices. The suspension system also enables pivoting movement of the surgical devices in the manner described below.

Figure 7:
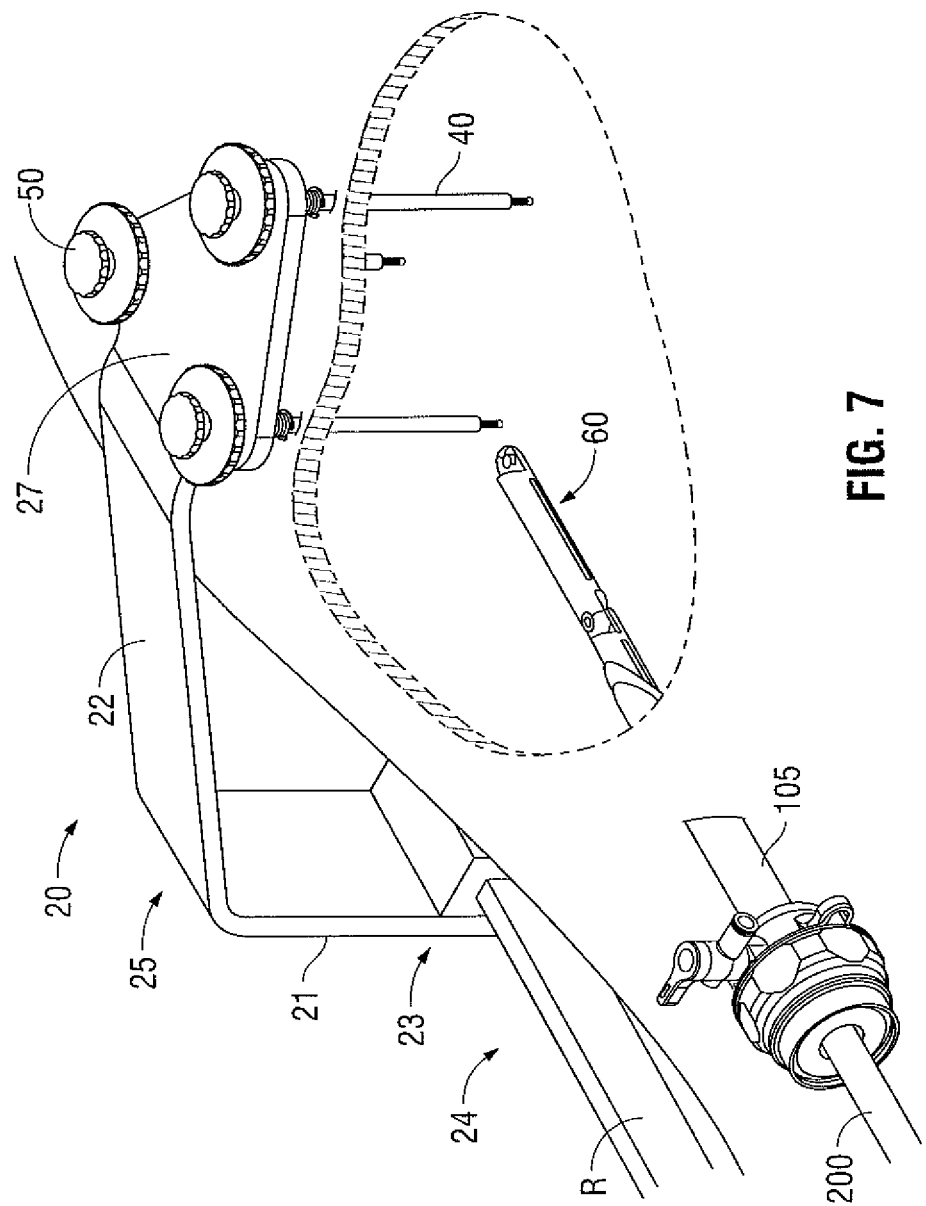
FIG. 7 is a partially cut away view of the suspension system illustrating insertion of the internal platform inside a body cavity.

The suspension system 10 includes an external frame structure 20, a plurality of elongated members or rods 40, and an internal platform 60. As shown in FIG. 7, the external frame structure 20 has a clamp 23, a vertical arm 21, and a horizontal arm 22. The clamp 23 is located at a lower end 24 of the vertical arm 21. The clamp is preferably configured to mount to the rail R of the operating table. The arms 21, 22 can be monolithic/integral or separate attached components. The horizontal arm 22 extends from an upper end 25 of the vertical arm 21 to overlie the patient.

In alternate embodiments, instead of vertical and horizontal arms, the arms can be curved. Additionally, a single curved or angled arm could alternatively be provided.

The arm(s) can be attached to the rail of the operating table, mounted to the floor, or mounted to other structure.

It is also contemplated that the arms 21 and 22 (or other alternate arms) could be pivotally or hingedly joined to one another. It will be understood that throughout this specification such joints between various members could be joints with additional degrees of rotational or translational freedom such as ball joints, telescoping joints and the like. This would enable the external platform 27 of the external frame structure 20 to be positioned at various angles with respect to the patient. For example, the platform 27 could be positioned generally horizontal with respect to the patient as shown in FIG. 7 as well as pivoted to acute angles or even pivoted to the side of the patient to a vertical position. Examples of systems with such movement are described below with reference to FIGS. 8A-12. Such adjustability would increase the versatility of the system. Locking mechanisms could also be provided to lock the arm in the desired angular position.

Referring back to FIGS. 1, 2 and 7, a plurality of threaded through holes 26 are formed in platform (mounting region 27) of horizontal arm 22 which is located at an opposite end from the vertical arm 21. Note that platform 27 can be pivotally or hingedly attached to arm 22 or can be integral/monolithic with arm 22. The platform 27 forms an external support. As shown, platform 27 is a substantially triangular region which supports the internal platform 60 in a substantially triangular configuration to support and maneuver surgical devices in the manner described below. Although shown as substantially triangular, other configurations are also contemplated, e.g. circular, oval, rectangular and other polygons.

Each of the plurality of threaded holes 26 of the region 27 are sized to provide passage of one of the rods (elongated members) 40 therethrough which secure the internal platform 60 (FIG. 1). As shown, the holes 26 are spread apart and preferably positioned at the vertices of the triangular region 27. Positioning in other areas is also contemplated as are a fewer or greater number of holes 26 to accommodate a different number of rods 40 if desired.

Figure 2:
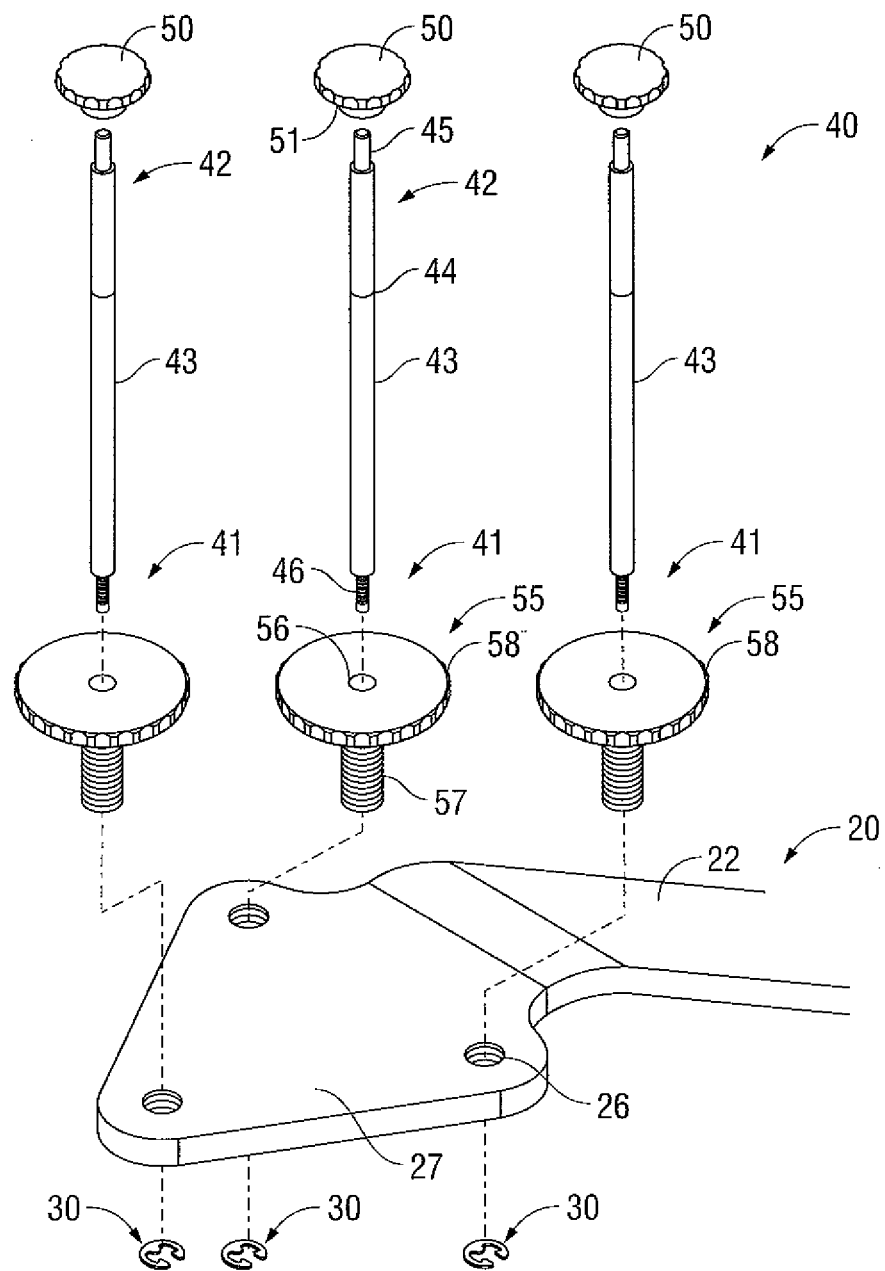
FIG. 2 is an exploded view of the external frame structure and the plurality of rods.

With reference to FIG. 2, each rod 40 includes a proximal portion 42, a distal portion 41, and a rod body 43 therebetween. Attached to the proximal portion 42 of the rod 40 is a knob 50 that mates with a restricted (reduced diameter) section 45 of the rod 40. The knob 50 may have a gripping surface 51 that increases the surface area and creates a leverage point for rotational interaction. For clarity, only one of the three rods 40 is fully labeled. Rotation of the knob 50 threading!}' (and removably) attaches the rod 40 to the internal platform 60 via engagement of threads 46 on the distal end of the rod 40 with the platform openings as described below.

A circumferential groove 44 is located in an intermediate region of the rod body 43, i.e. distal of the knob 50 and proximal of the distal portion 41. The groove 44 is sized to accept a retaining ring 30. The combination of the knob 50 and the retaining ring 30 restricts axial movement of the rod body 43 within a central aperture 56 of screw 55, while allowing rotational movement. Rod 43 is rotated to thread into the internal platform 60 in the manner described below.

Each screw 55 has external threads 57 that mate with one of the plurality of internally threaded holes 26 in the external platform region 27 of frame structure 20. The screw 55 preferably includes knurls 58 to provide rotational interaction for threading the screw 55 into the holes 26. Screw 55 can be used to advance or retract the rod 40 which moves the internal platform 60 as described in detail below. That is, rotation of screw 55 in a first direction, presses knob 50 in an upward direction to lift the associated (connected) region of the internal platform 60. Rotation of screw 55 in an opposite direction presses retaining ring 30 in a downward direction to return the associated (connected) region of the internal platform 60 to its original position. Thus, the range of movement in this embodiment is defined as a distance between these components which in one embodiment can be about 0.5 inches, although other distances are also contemplated. This adjustment allows a microadjustment of the platform position by warping any or all of the rods 40.

Figure 3:
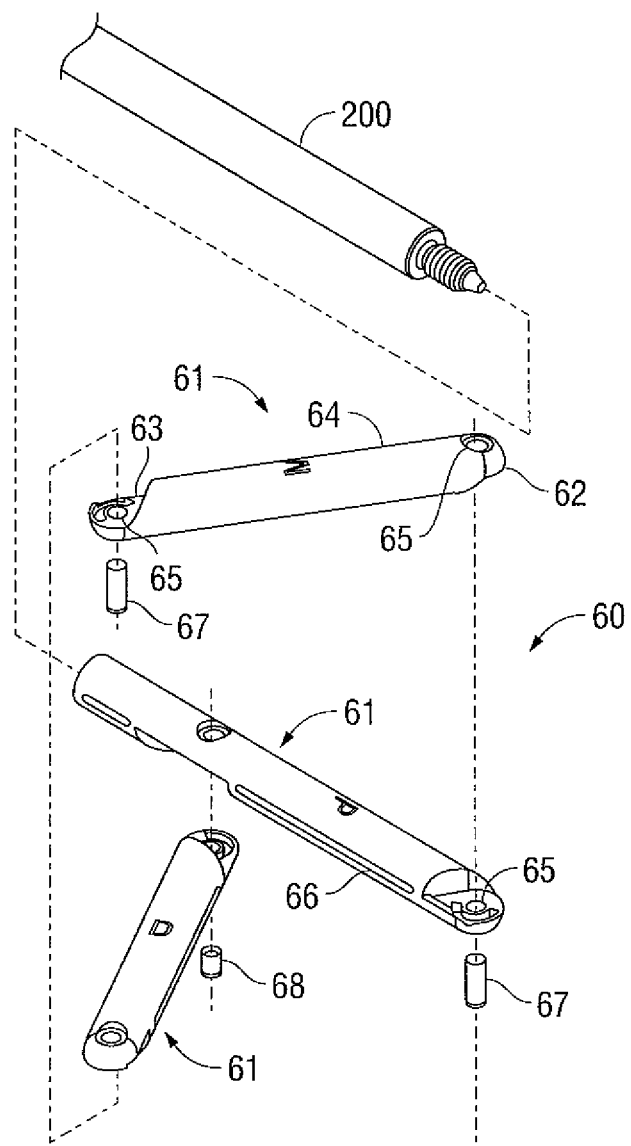
FIG. 3 is an exploded view of the internal platform and an insertion tool for the platform.
Figure 5:
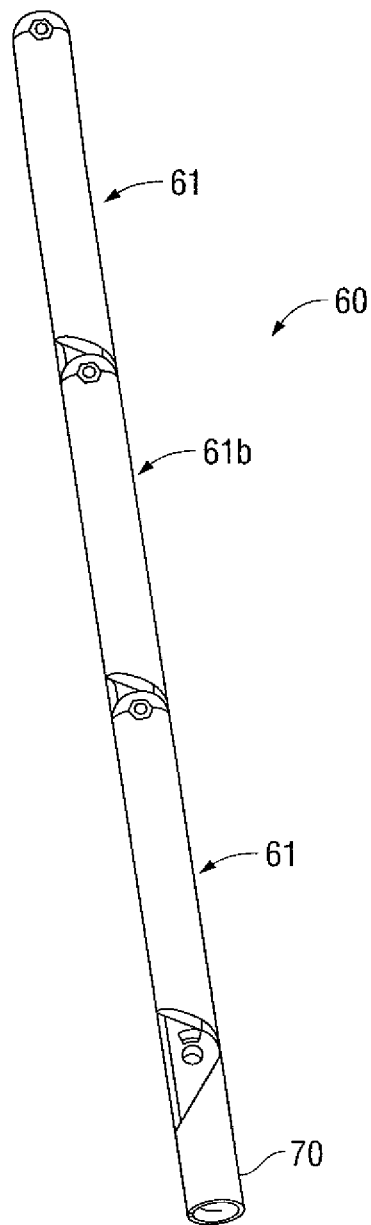
FIG. 5 is a perspective view of the internal platform in a fully extended (elongated) position for insertion to the body cavity.
Figure 6:
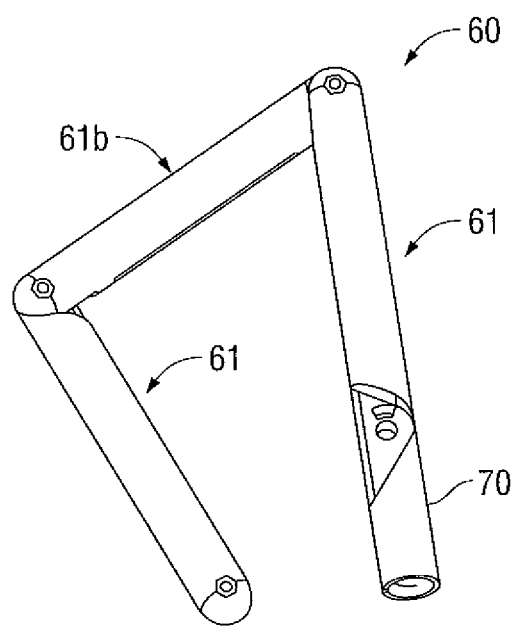
FIG. 6 is a perspective view of the internal platform in a partially angled (pivoted) position.

Now referring to FIGS. 3, 5, and 6, the internal platform 60 includes a series of interconnecting links 61 having a first mating end 62, a second mating end 63, and a link body 64 therebetween. These links form a rigid support inside the patient's body cavity. In the illustrated embodiment, three links 61 are provided to form a substantially triangular region. However, a different number of links can be provided and the links can be arranged in different shapes, e.g. circular, oval, rectangular or other shapes including other polygonal shapes. Each end 62 of link 61 is connectable with the end 63 of another of the series of links 61. Each of the series of interconnecting links 61 has a pair of holes 65. One of the pair of holes 65 is located at each end of the link 61, e.g. in the end 63 and end 62. Each of the pair of holes 65 provides passage of the threaded section 46 of the rod 40 therethrough to enable the rod 40 to be removably attached to the platform 60 and enable the rod 40 to be rotated to change the plane of the associated link 61 and thereby change the plane of the internal platform 60.

The internal platform 60 includes two different sized bushings: a longer bushing 67 and a shorter bushing 68. The longer bushing 67 connects the ends 62 and 63 of at least two links 61 together by an interference fit to form the series of links 61 in a non-linear configuration, such as the illustrated substantially triangular configuration. The shorter bushing 68 extends only through the initial hole 65 in the series of links 61. Each of the bushings 67 and 68 may have a complementary thread to that of the threaded section 46 of the rod 40 that allows the rod 40 to be secured to the internal platform by rotation of the knob 50. Alternatively, it is also contemplated that the bushings 67 and 68 be unthreaded and that a separate nut (not shown) is used to secure the platform 60 to the rod 40. Further contemplated are the use of snap together links (not shown).

Each of the links 61 can include a slot 66 located along the link body 64 thereof, and extending longitudinally along the link 61, which can accommodate a pull cable for pivoting the links.

The suspension system 10 includes a pod 110 (FIG. 8) with a complementary attachment structure 115 that provides attachment to the links 61. The attachment structure can include a threaded structure, a snap on feature, one or more magnets, or other structure. The pod 110 may include a surgical instrument that is a visualization device such as a camera 111 or an illumination source 112. Other surgical instruments that are contemplated include, but are not limited to, a grasper, a retractor, and a sensor.

Figure 4:
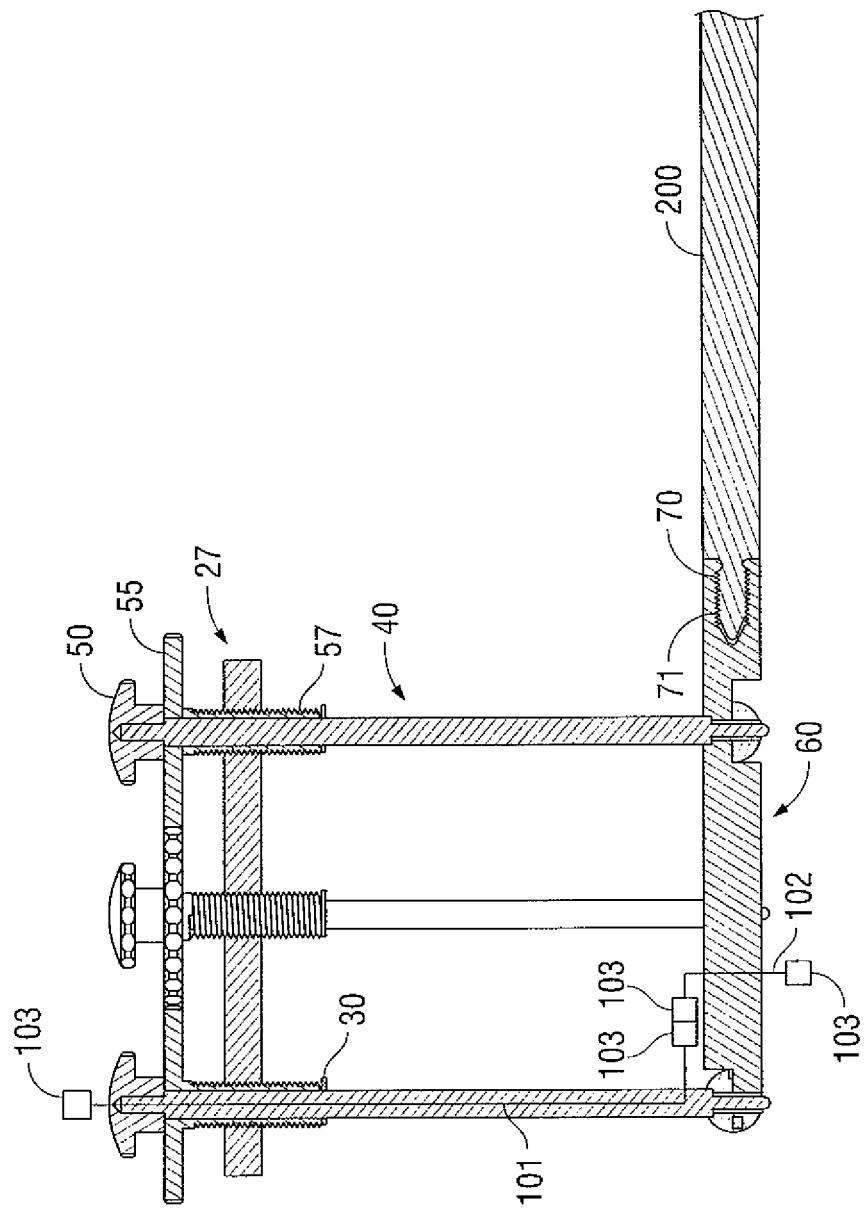
FIG. 4 is a side cross-sectional view of the suspension system of FIG. 1 taken along section line 4-4 of FIG. 1.

Now referring to FIG. 4, at least one of the rods 40 may contain an electrical conduit 101 that may be connected with a second electrical conduit 102 located in at least one of the links 61. Each of the conduits 101, 102 has an electrical connector 103 on each end of the conduit. The connectors 103 may be either internal to the components 40, 61, or the connectors may be located external to the components 40, 61. The electrical conduits 101, 102, in combination with the electrical connector 103, provide communication between a remote control unit (not shown) and instruments coupled to the internal platform 60. Specifically, these electrical connections may provide one or more of the following: (a) electrical power; (b) control signals; and (c) optical information (e.g. light and/or video signals).

Other arrangements of the electrical connectors are also contemplated. For example, the connectors can be coaxially positioned in a single rod, they can be positioned in separate rods, or can be positioned parallel within a non-conductive rod.

At least one of the links 61 preferably has a tool receiving section 70 (FIGS. 5 and 6) for placing the internal platform 60 within the body cavity. The insertion tool receiving section 70 may have either internal or external threads 71 that mate with the end of a tool or driver 200 for placement of the internal platform 60 through a cannula 105, as shown in FIG. 7. Alternatively, other disengagable retention structure for tool 70 and link 61 can be provided such as a bayonet lock.

For delivery, the links 61 are in an elongated position, substantially aligned with the longitudinal axis passing through the series of links. In this substantially linear position, they can be delivered through a trocar or access port inside the body cavity (see e.g. cannula 105 of FIG. 7). Once delivered, the links 61 are manipulated to a second position, wherein the links 61 are pivoted to an angular or non-linear position, and preferably form a substantially triangular configuration. This region preferably corresponds to the region 27 of arm 22 of external frame structure 20. In this manner, the openings 65 in the links 61 are substantially aligned with holes 26 of platform region 27 for reception of elongated rods 40.

The links 61 can be pivoted by the delivery tool 200 in a hinge like manner to form the triangular shape (or other shapes). Alternatively, a pull wire (not shown) can be provided within a slot 66 in the links which is tensioned to pivot the links to their angled mounting position. In another variation, the links are spring loaded to a substantially triangular or other non-linear position and a wire extending through the links maintains the links in an elongated position. As the wire is retracted from the links, the links return to their spring biased position.

The elongated rods 40 are attached to the internal platform region 27 of the external frame 20 as described above. Consequently, at least the distal portions of the rods 40 extend within the body cavity. As shown, the rods 40 extend substantially parallel to one another as they extend into the body cavity, although the internal platform 60 could alternatively enable mounting of the instruments in angled positions.

Figure 8:
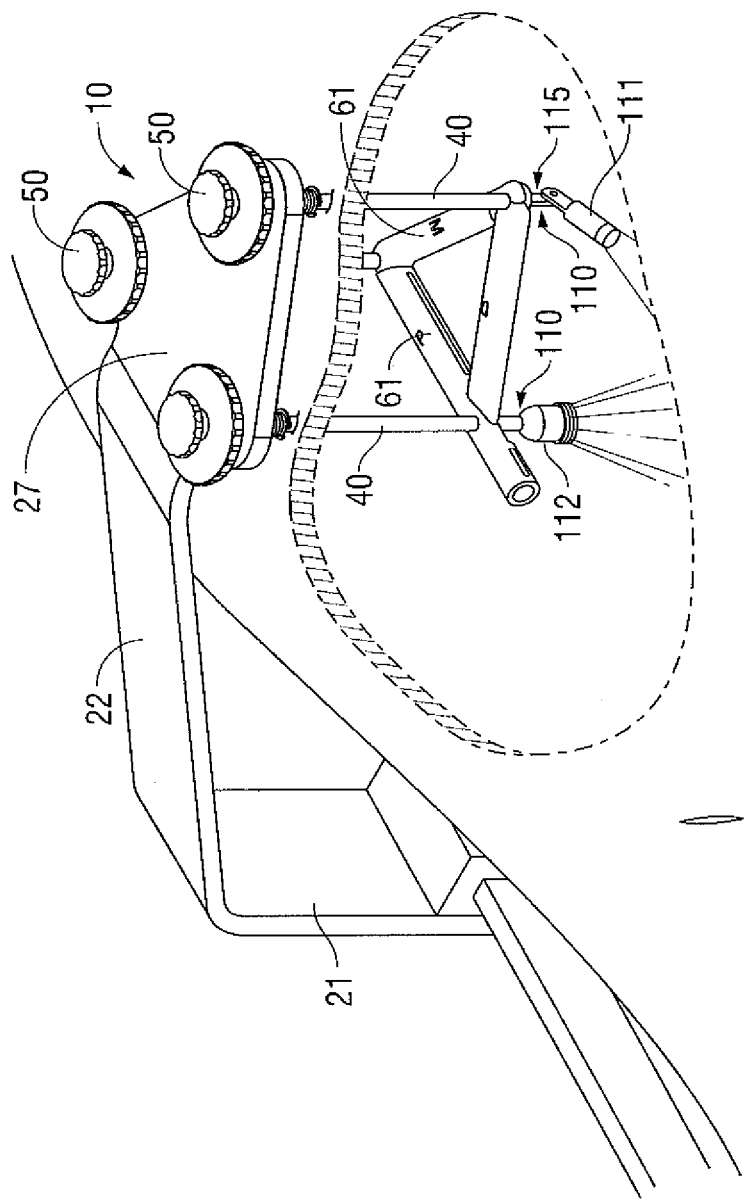
FIG. 8 is a partially cut away view of the suspension system including a camera and an illumination source attached to the internal platform.

With the rods 40 extending into the body cavity, when the links 61 are delivered, the opening in the distalmost link 61 is mated with the distal threaded portion 46 of a rod 40. The insertion tool 200 is then manipulated to pivot the intermediate link 61b with respect to the distalmost link 61 and then attached to a second rod 40. The proximal link 61 is then pivoted with respect to the intermediate link, for attachment to the third elongated rod 40, thus forming the aforedescribed substantially triangular shape. The insertion tool 200 can then be withdrawn through the cannula 105, leaving the cannula 105 free for insertion of other instruments. A laparoscopic imaging device, e.g. a camera, wired or cordless, can then be inserted for example through cannula 105 and attached to the internal platform 60 as described above. An illumination device can also be inserted through the cannula 105 and attached to the internal platform 60. This is shown in FIG. 8. A third device can be inserted through cannula 105 and attached to the internal frame as well. Note that instruments other than or in addition to the camera and illuminator can be inserted and attached to the internal frame 60. In embodiments with additional attachment structure, more devices can be inserted and attached.

Once mounted, the instruments can be maneuvered by manipulation of the rods 40. More specifically, rotation of the screw 55 in a first direction will cause retraction of the rod 40 which in turn will cause retraction of the link 61 to which it is attached. As the links are connected in a substantially triangular region, such retraction causes the respective vertex of the internal platform 60 to retract as the other vertices remain stationary, thereby lifting a portion of the internal platform 60 out of the plane. As can be appreciated, any one of the vertices can be moved with respect to the other two, as well as two of the vertices can be moved with respect to the other vertices, thus providing a conical shaped range of movement. In this manner, maneuverability of the instruments is achieved while maintaining a stable and substantially rigid suspension system as the internal platform 60 is connected to the external platform 27 which is mounted to the operating table (or the floor).

In embodiments wherein the external platform 27 is movably, e.g. pivotably, mounted to an external supporting frame, the screws 55 can be used for fine adjustment of internal platform 60 and the pivotal movement of the external platform 27 used for coarse adjustment as the pivotal movement will move the respective rod(s) 40 which in turn will move the internal platform 60. Such pivotable mounting is illustrated in FIGS. 8A-12.

FIGS. 8A-12 illustrate embodiments of the suspension system providing for pivotable or rotatable movement of the external frame, or portion thereof. Turning first to FIG. 8A, the suspension system 110 is identical to the suspension system 10 of FIG. 1 except for the attachment of the platform. More specifically, the suspension system 210, like suspension system 10, includes an external frame structure 220, a plurality of elongated members or rods 240 with knobs 250 and screws 255, and an internal platform 260. The internal platform 260 includes a series of interconnecting links 261 identical to links 60 of the embodiment of FIG. 1. For brevity, details of the structure and function of these components of FIG. 8A will not be repeated herein as they are identical to that described above in the embodiment of FIGS. 1-8. Only the differences between the embodiment of FIG. 8A and FIG. 1 will be discussed. The difference is in the attachment of horizontal arm 222 to vertical arm 221.

More specifically, horizontal arm 222 is pivotably attached to vertical arm 221 at hinge 223. This enables the horizontal arm 222 to pivot in the direction of the arrow of FIG. 8A which in turn moves the external platform 227. One such pivoted position is illustrated in phantom in FIG. 8A, it being understood that preferably various angled positions can be achieved. Further, as previously discussed, the hinge may be a ball and socket joint allowing additional angular adjustments. Preferably the hinged structure maintains the external platform 227 in the selected angled position. However, mechanisms to lock the external platform 227 in a selected position are also contemplated. Movement of the external platform 227 moves the connected rods 240 which in turn move the connected internal platform (links 260) to change the angle of the instrumentation attached to the internal platform.

Figure 9:
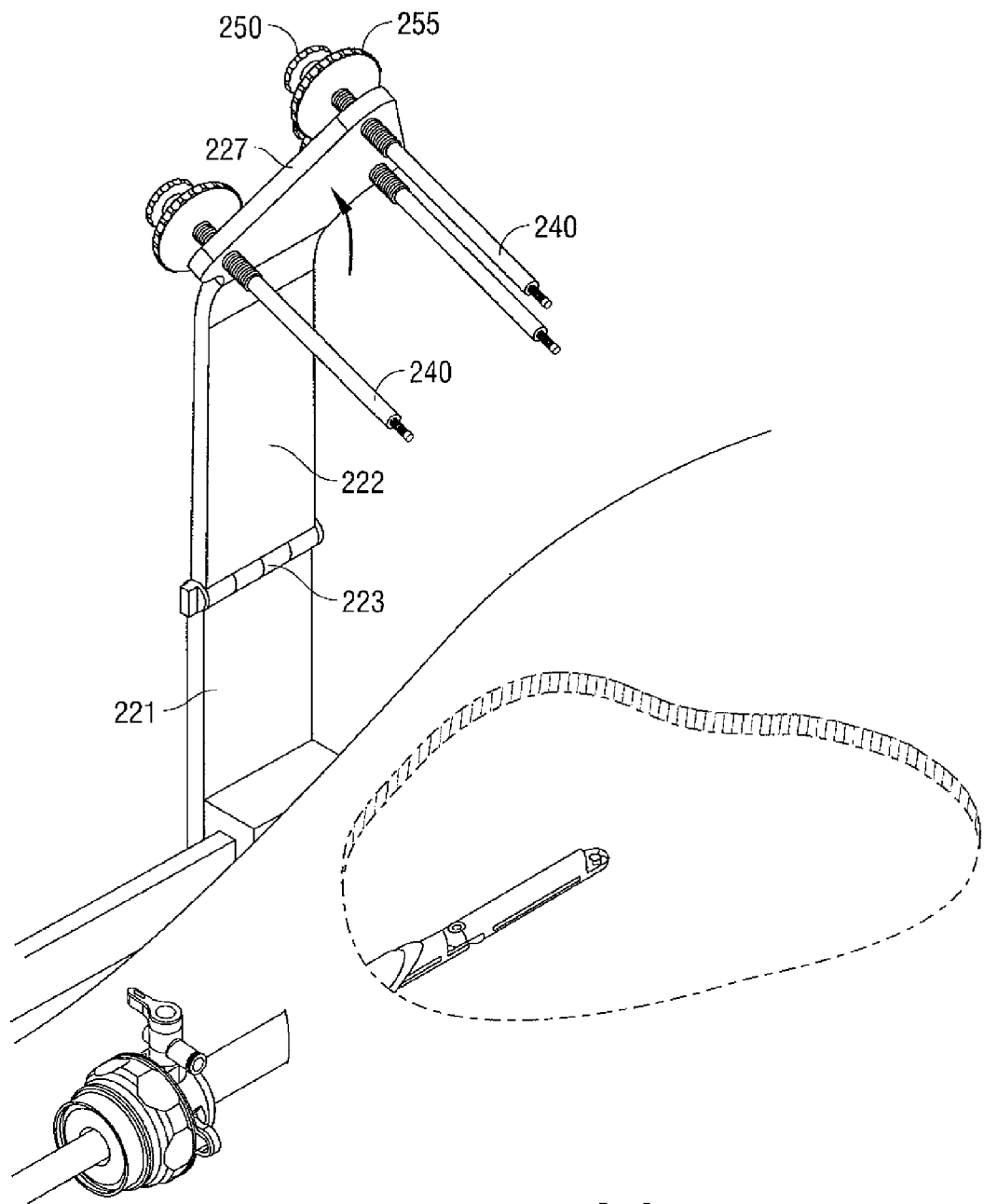
FIG. 9 illustrates movement of the external frame structure to a vertical position.

The foregoing structure can also be provided such that the horizontal arm 222 can be pivoted from a horizontal position overlying the patient's incision to a vertical position, substantially aligned with a longitudinal axis of the vertical arm 221 as shown in FIG. 9. This can move the system away from the patient and out of the way of the surgeon until positioning over the patient is desired.

Figure 10:
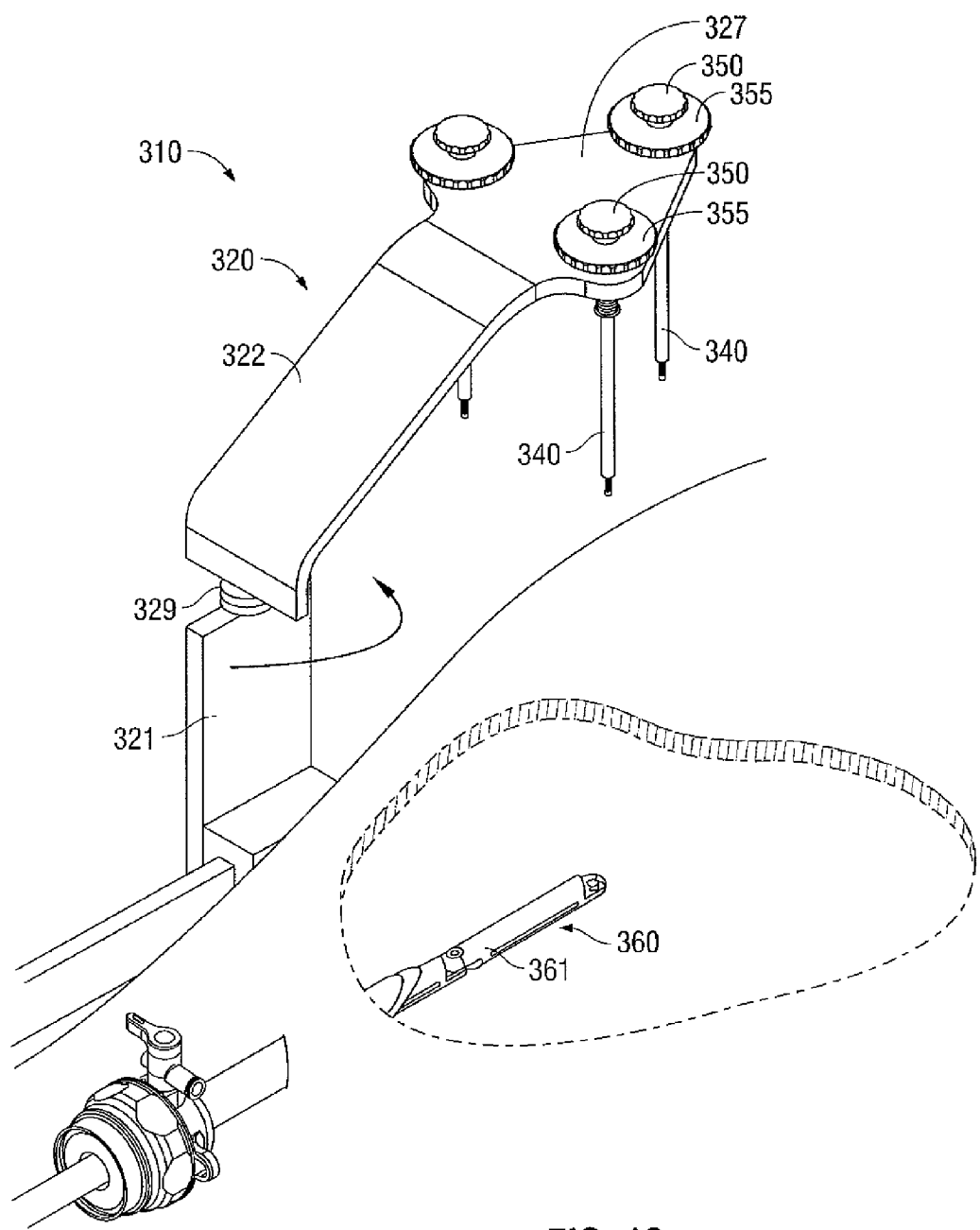
FIG. 10 is a partially cut away view of an alternate embodiment of the suspension system illustrating a swivel attachment of the external frame to rotate the external frame away from the patient.

In another alternate embodiment illustrated in FIG. 10, suspension system 310 is identical to suspension system 10 of FIG. 1 except for the pivoting attachment of horizontal arm 322 to vertical arm 321. Thus, the suspension system 310, like suspension system 10, includes an external frame structure 320, a plurality of elongated members or rods 340 with knob 350 and screw 355, and an internal platform 360. The internal platform includes a series of interconnecting links 361 identical to links 60 of the embodiment of FIG. 1. For brevity, details of the structure and function of these components will not be repeated herein as they are identical to that described above in the embodiments of FIGS. 1-8. Only the differences between the embodiment of FIG. 10 and FIG. 1 will be discussed. The difference is in the attachment of horizontal arm 322 to vertical arm 321.

Pivot fastener 329 enables the horizontal arm 322 to be rotated (swiveled) in the direction of the arrow to pivot about a longitudinal axis of the vertical arm 321. Such pivotal movement of the external platform 327 moves the internal platform 360, thereby changing the lateral position of the instruments attached to the internal platform 327. As shown in FIG. 10, the horizontal arm 322 can be pivoted (swiveled) a sufficient amount to move the suspension system 210 out of the way of the surgeon. Rotation of 360 degrees or less is contemplated. The pivot can be configured so the horizontal arm 322 remains in the selected position. The pivot can also be configured so that the arm 322 can also move up and away from patient and down toward the patient.

Figure 11:
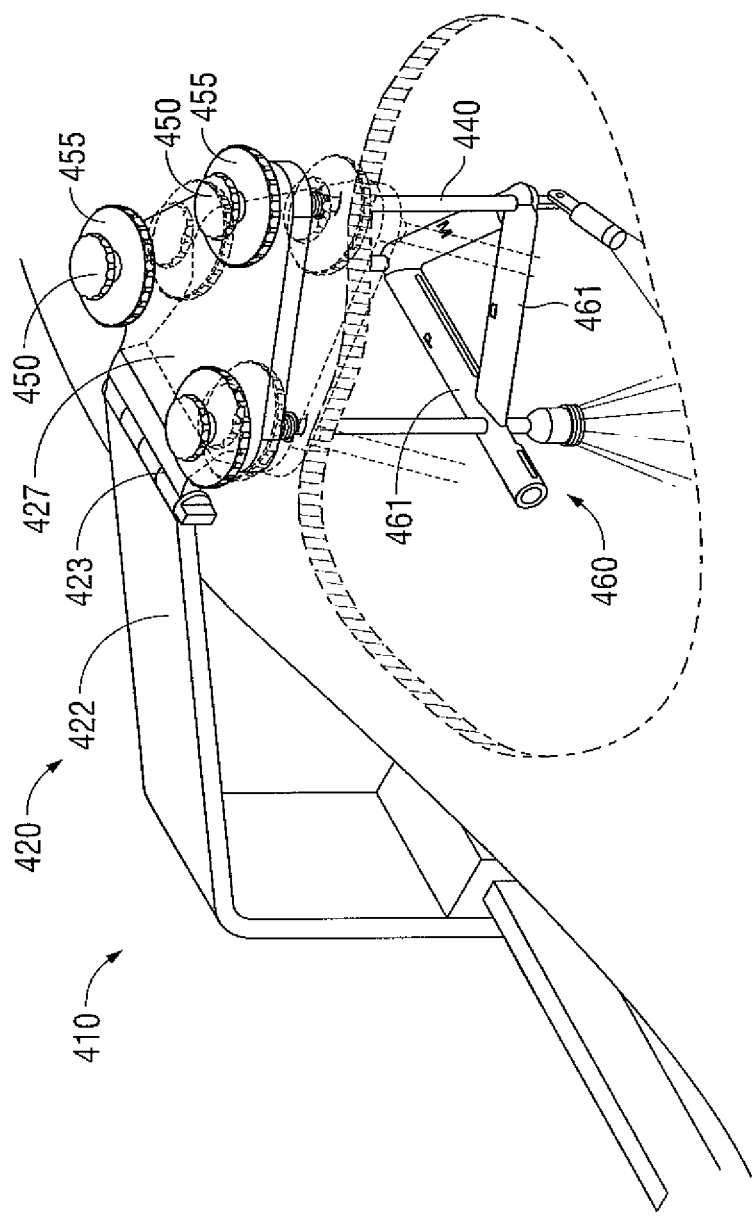
FIG. 11 is a partially cut away view of another alternate embodiment the suspension system including a camera and an illumination source attached to the internal platform and showing in phantom movement (exaggerated for clarity) of the connecting rods.
Figure 12:
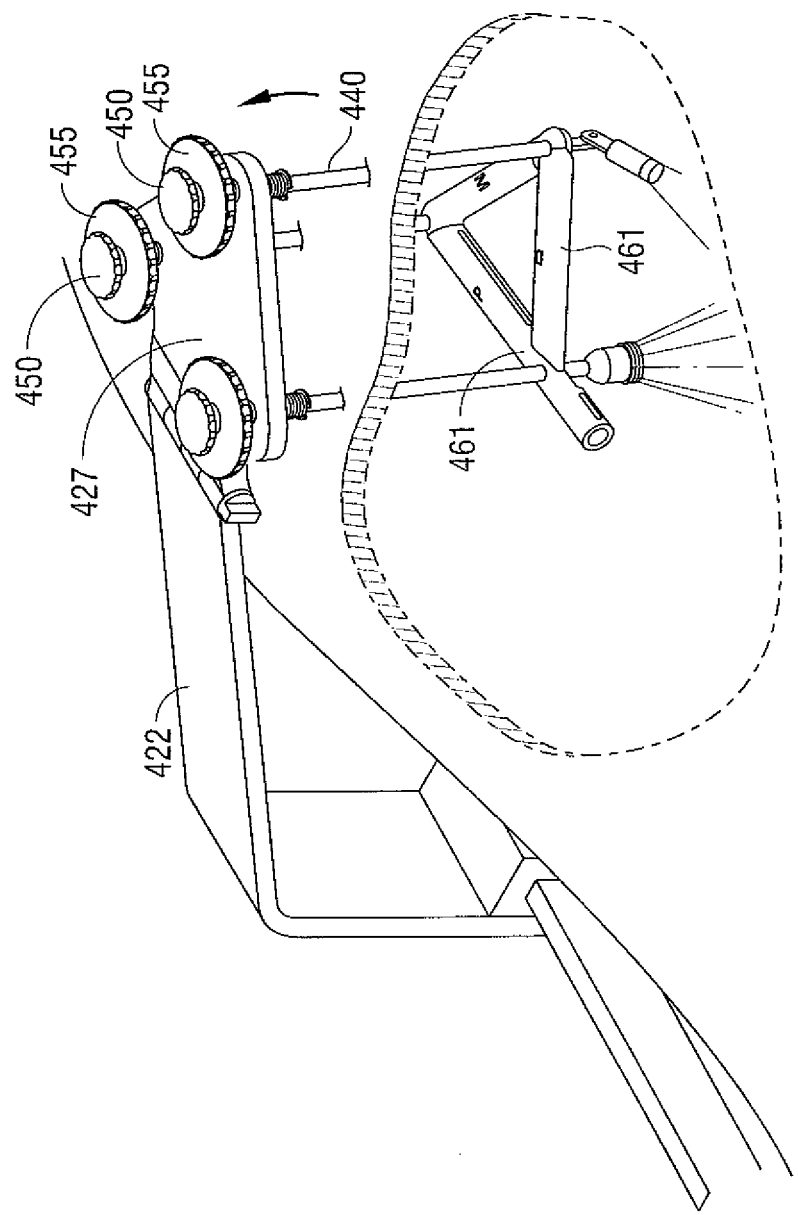
FIG. 12 is a partially cut away view of the suspension system of FIG. 11 including a camera and an illumination source attached to the internal platform and showing pivoting of the external frame.

The alternate embodiment of FIGS. 11 and 12 are identical to FIG. 1 except that the hinge 423 for enabling pivoting of the external platform 427 is at the end of the horizontal arm 422. Otherwise, the suspension system 410 is identical to suspension system 10 and includes an external frame structure 420 with external platform 427, a plurality of elongated members or rods 440 with knobs 450 and screws 455, and an internal platform 460. The internal platform 460 includes a series of interconnecting links 461 identical to links 60 of the embodiment of FIG. 1. For brevity, details of the structure and function of these components will not be repeated herein as they are identical to that described above in the embodiments of FIGS. 1-8. Only the differences between the embodiment of FIG. 11 and FIG. 1 will be discussed. The difference is in the attachment of external platform 427 to horizontal arm. FIG. 11 illustrates in phantom a pivoted position of the elongated rods 440 (as a result of pivoting external platform 427) which in turn would pivot the internal platform 460 to change the position of the instruments extending therefrom.

The systems described herein also provide reference points to measure the position and orientation of the instrument. For example, measurement lines can be provided on the screw 55 to measure the lift or angle of the internal platform. A transducer at the screw 55 can also be used for measurement.

The present disclosure also relates to a method for providing a stable platform for surgical instruments for performing minimally invasive surgery, e.g. laparoscopic surgery. In the method, which by way of example describes the system of FIG. 1, it being understood that the other systems would be used in a similar manner, elongated members or rods 40 are connected to the external frame 20 and are inserted into a body cavity of a patient. The internal platform 60 is inserted through a different port site in a substantially straight position. The internal platform is then reconfigured inside the body cavity to a non-linear configuration and the elongated members (segments) are joined to the platform inside the body cavity.

It is also contemplated that instead of having the elongated members linked together outside the body, they can be inserted one at a time through a port site and connected to each other in situ to form the desired internal platform shape.

The suspension system 10 may be provided in either kit form or as individual pieces.

After the selected instruments are coupled to the internal platform 60, the physician performs the desired surgical procedure in the working space. Once the surgical procedure is completed, the physician removes the surgical instruments and the platform 60 by reversing the above-described installation technique. Note that the surgeon can pivot the external platform to change the position of the internal platform which in turn alters the angle of the surgical instrumentation if the systems of FIGS. 8A-12 are utilized.

It will be understood that various modifications may be made to the embodiments disclosed herein. For example, the size, angles, curves, and/or attachment means of the component(s) surface(s) may be modified to better suit a particular surgical procedure. Therefore, the above description should not be construed as limiting, but merely as exemplifications of various embodiments. Those skilled in the art will envision other modifications within the scope and spirit of the claims appended hereto.

What is claimed is:

1. A suspension system for supporting surgical devices inside a patient's body cavity, the suspension system comprising:
   an external frame having a first support and a second support;
   a plurality of elongated members extending from the external frame and into the body cavity; and
   an internal platform located inside the body cavity, the internal platform including a plurality of links reconfigurable from a first elongated position wherein the links are substantially aligned along a longitudinal axis for insertion to a second position wherein the links are angled with respect to one another to form a non-linear configuration, the first support being movable with respect to the second support to thereby move the internal platform, each elongated member having a proximal portion and a distal portion, wherein the external frame includes a first attachment structure for connecting with the proximal portion of one of the elongated members, and each link includes a second attachment structure configured to receive the distal portion of one of the elongated members.

2. The suspension system of claim 1, wherein the first support comprises an elongated arm pivotably attached to the second support for movement toward and away from the body cavity.

3. The suspension system of claim 1, wherein the first support comprises an elongate arm rotatably attached to the second support for rotation about an axis of the second support.

4. The suspension system of claim 1, wherein the elongated members are adjustably attached to the external frame.

5. The suspension system of claim 1, wherein the links each include an opening, the elongated members extending through the respective openings such that the distal end of the respective elongated members protrudes distally from the respective openings, the links each having mounting structure for mounting a surgical device thereto.

6. The suspension system of claim 1, wherein the links are pivotally attached to one another.

7. The suspension system of claim 1, wherein the first support is pivotable from a position substantially horizontal to overlie the patient to a position substantially vertical with respect to the patient.

8. The suspension system of claim 1, wherein one of the links has a tool attachment structure for detachable connection to an insertion tool.

9. A suspension system for supporting surgical devices inside a patient's body cavity, the suspension system comprising:
   an external frame having a plurality of holes extending therethrough, the external frame being movably connected to a support for movement with respect to the body cavity;
   a plurality of rods extending from the external frame, each of the plurality of rods being sized to at least partially extend through one of the plurality of holes; and
   an internal platform including a series of interconnecting links, each of the series of interconnecting links having at least one hole sized to receive one of the rods therethrough, wherein the links are reconfigurable between a generally elongated position and an angular position within the body cavity.

10. The suspension system of claim 9, wherein each of the links includes an attachment structure located therealong.

11. The suspension system of claim 9, further comprising a pod, the pod having an attachment structure complementary to an attachment structure of the links.

12. A suspension system for supporting surgical devices inside a patient's body cavity, the system comprising:
   a substantially rigid external frame positioned outside the body and movably connected to an external support for movement with respect to the body cavity;
   a plurality of elongated connectors extending from the external frame into the body cavity; and
   an internal support located inside the body cavity and attached to the elongated connectors, the elongated connectors movable to apply a retraction force on a portion of the internal support to change a plane defined by the portion with respect to other portions of the internal support, wherein the internal support includes a plurality of links reconfigurable from a first position wherein the links are substantially aligned along a longitudinal axis for insertion to a second position wherein the links are angled with respect to one another to form a non-linear configuration for attachment to the elongated connectors.

13. The suspension system of claim 12, wherein the external frame is connected to an operating table.

14. The suspension system of claim 13, wherein the external frame is vertically adjustable with respect to the operating table.

15. The suspension system of claim 13, wherein the internal support has an instrument receiving structure to mount surgical instruments thereto.

16. The suspension system of claim 12, wherein the external support remains in a fixed plane position as the portion of the internal support is retracted.

17. The suspension system of claim 12, further comprising an adjustment member to adjust a position of the elongated connector, the adjustment member providing for fine adjustment and the movement of the external frame applying coarse adjustment of the position of the elongated connector.

* * * * *